US012589030B2

(12) United States Patent (10) Patent No.: US 12,589,030 B2
Bigler et al. (45) Date of Patent: Mar. 31, 2026

(54) APPARATUS AND METHODS FOR TREATING EXCESS INTRAOCULAR FLUID

(71) Applicant: ECOLE POLYTECHNIQUE FEDERALE DE LAUSANNE (EPFL), Lausanne (CH)

(72) Inventors: Stephane Bigler, Leysin (CH); Nikolaos Stergiopulos, Preverenges (CH)

(73) Assignee: Ecole Polytechnique Federale De Lausanne, Lausanne (CH)

( * ) Notice: Subject to any disclaimer, the term of this patent is extended or adjusted under 35 U.S.C. 154(b) by 0 days.

(21) Appl. No.: 18/359,838

(22) Filed: Jul. 26, 2023

(65) Prior Publication Data

US 2024/0091063 A1 Mar. 21, 2024

Related U.S. Application Data

(63) Continuation of application No. 16/826,858, filed on Mar. 23, 2020, now Pat. No. 11,712,371, which is a
(Continued)

(51) Int. Cl.
*A61F 9/00* (2006.01)
*A61F 9/007* (2006.01)
(Continued)

(52) U.S. Cl.
CPC ............ *A61F 9/00781* (2013.01); *A61F 9/00* (2013.01); *A61F 9/0008* (2013.01);
(Continued)

(58) Field of Classification Search
CPC ...... A61F 9/00; A61F 9/0008; A61F 9/00736; A61F 9/00781; A61M 2210/0612; A61M 27/002
See application file for complete search history.

(56) References Cited

U.S. PATENT DOCUMENTS 3,159,161 A * 12/1964 Ness ................... A61F 9/00781
623/4.1
3,863,067 A 1/1975 Gooley
(Continued)

FOREIGN PATENT DOCUMENTS

EP 1243826 A2 9/2002
EP 1484535 A1 12/2004
(Continued)

OTHER PUBLICATIONS

International Preliminary Report on Patentability dated Jul. 25, 2013 in Int'l PCT Patent Appl No. PCT/EP2012/050455, 8 pages.
(Continued)

*Primary Examiner* — Kai H Weng
(74) *Attorney, Agent, or Firm* — Greenberg Traurig, LLP; Christopher C. Bolten; Albert K. Heng

(57) ABSTRACT

An ocular drainage system is provided for treating diseases that produce elevated intraocular pressures, such as glaucoma, wherein the system includes an implantable device and an external control unit, the implantable device includes a non-invasively adjustable valve featuring at least one deformable tube and a disk rotatably mounted within a housing, such that rotation of the disk using the external control unit causes the disk to apply a selected amount of compression to the deformable tube, thereby adjusting the fluidic resistance of the deformable tube and regulating the intraocular pressure.

19 Claims, 8 Drawing Sheets

Related U.S. Application Data continuation of application No. 15/600,597, filed on May 19, 2017, now Pat. No. 10,603,214, which is a continuation-in-part of application No. 14/819,286, filed on Aug. 5, 2015, now Pat. No. 9,655,779, which is a continuation of application No. 13/349,353, filed on Jan. 12, 2012, now Pat. No. 9,101,445.

(60) Provisional application No. 61/433,131, filed on Jan. 14, 2011.

(51) Int. Cl.

| | |
|---|---|
| *F04B 43/04* | (2006.01) |
| *F04B 43/09* | (2006.01) |
| *F04B 43/12* | (2006.01) |
| *F04B 43/14* | (2006.01) |
| *A61M 27/00* | (2006.01) |

(52) U.S. Cl.
CPC .......... *A61F 9/00736* (2013.01); *F04B 43/04* (2013.01); *F04B 43/09* (2013.01); *F04B 43/1253* (2013.01); *F04B 43/14* (2013.01); *A61M 27/002* (2013.01); *A61M 2210/0612* (2013.01); *F04B 2201/1208* (2013.01)

(56) References Cited

U.S. PATENT DOCUMENTS

| | | | |
|---|---|---|---|
| 4,232,451 | A | 11/1980 | Thomsen |
| 4,457,757 | A | 7/1984 | Molteno |
| 4,554,918 | A * | 11/1985 | White ................ A61F 9/00781 |
| | | | 604/10 |
| 4,856,972 | A | 8/1989 | Van Benschoten et al. |
| 5,117,870 | A | 6/1992 | Goodale et al. |
| 5,300,020 | A | 4/1994 | L'Esperance, Jr. |
| 5,342,025 | A | 8/1994 | Hwang |
| 5,397,300 | A | 3/1995 | Baerveldt et al. |
| 5,411,473 | A | 5/1995 | Ahmed |
| 5,586,872 | A | 12/1996 | Skobelev et al. |
| 5,601,094 | A | 2/1997 | Reiss |
| 5,626,558 | A | 5/1997 | Suson |
| 5,882,327 | A | 3/1999 | Jacob |
| 6,050,970 | A | 4/2000 | Baerveldt |
| 6,077,299 | A | 6/2000 | Adelberg et al. |
| 6,168,575 | B1 | 1/2001 | Soltanpour |
| 6,186,974 | B1 | 2/2001 | Allan et al. |
| 6,251,090 | B1 | 6/2001 | Avery et al. |
| 6,261,256 | B1 | 7/2001 | Ahmed |
| 6,450,984 | B1 | 9/2002 | Lynch et al. |
| 6,508,779 | B1 | 1/2003 | Suson |
| 6,544,208 | B2 | 4/2003 | Ethier et al. |
| 6,589,198 | B1 | 7/2003 | Soltanpour et al. |
| 6,726,664 | B2 | 4/2004 | Yaron et al. |
| 7,093,818 | B2 | 8/2006 | Koeneman |
| 7,854,600 | B2 | 12/2010 | Ogawa |
| 8,702,639 | B2 | 4/2014 | Van Der Mooren et al. |
| 8,840,578 | B2 | 9/2014 | Dos Santos et al. |
| 9,101,445 | B2 | 8/2015 | Bigler et al. |
| 9,545,337 | B2 | 1/2017 | Yalamanchili et al. |
| 9,655,779 | B2 | 5/2017 | Bigler et al. |
| 10,039,670 | B2 | 8/2018 | Ilios et al. |
| 10,154,925 | B2 | 12/2018 | Ahmed et al. |
| 10,166,145 | B2 | 1/2019 | Ahmed et al. |
| 10,201,451 | B2 | 2/2019 | Camras et al. |
| 10,342,702 | B2 | 7/2019 | Camras et al. |
| 10,596,035 | B2 | 3/2020 | Stergiopulos et al. |
| 10,603,214 | B2 | 3/2020 | Bigler et al. |
| 12,274,643 | B2 | 4/2025 | Stergiopulos et al. |
| 2002/0087111 | A1 | 7/2002 | Ethier et al. |
| 2004/0162545 | A1 | 8/2004 | Brown et al. |
| 2005/0053501 | A1 | 3/2005 | Akahori |
| 2005/0256447 | A1 | 11/2005 | Richardson et al. |
| 2006/0175357 | A1 | 8/2006 | Hammond |
| 2007/0154336 | A1 | 7/2007 | Miyazaki et al. |
| 2009/0099626 | A1 | 4/2009 | de Juan, Jr. et al. |
| 2009/0208350 | A1 | 8/2009 | Miyazaki et al. |
| 2010/0010416 | A1 * | 1/2010 | Juan, Jr. ................ A61B 34/70 |
| | | | 604/9 |
| 2010/0114006 | A1 | 5/2010 | Baerveldt |
| 2010/0249691 | A1 | 9/2010 | Van Der Mooren et al. |
| 2010/0321345 | A1 | 12/2010 | Pearce et al. |
| 2011/0066098 | A1 | 3/2011 | Stergiopulos |
| 2012/0184892 | A1 | 7/2012 | Bigler et al. |
| 2013/0150775 | A1 | 6/2013 | Dos Santos et al. |
| 2013/0150779 | A1 | 6/2013 | Field |
| 2013/0211312 | A1 | 8/2013 | Gelvin |
| 2013/0317413 | A1 | 11/2013 | Field et al. |
| 2017/0348149 | A1 | 12/2017 | Stergiopulos et al. |
| 2017/0348151 | A1 | 12/2017 | Ahmed et al. |
| 2021/0275356 | A1 | 9/2021 | Stergiopulos et al. |

FOREIGN PATENT DOCUMENTS

| | | |
|---|---|---|
| JP | S547791 A | 1/1979 |
| JP | H06509732 A | 11/1994 |
| JP | H10503405 A | 3/1998 |
| JP | 2004340184 A | 12/2004 |
| WO | WO-9112037 A1 | 8/1991 |
| WO | WO-9303778 A1 | 3/1993 |
| WO | WO-9603944 A1 | 2/1996 |
| WO | WO-9962586 A1 | 12/1999 |
| WO | WO-9966862 A1 | 12/1999 |
| WO | WO-2009066133 A1 | 5/2009 |
| WO | WO-2013090197 A1 | 6/2013 |
| WO | WO-2014036437 A1 | 3/2014 |
| WO | WO-2018009556 A1 | 1/2018 |
| WO | WO-2020049508 A1 | 3/2020 |

OTHER PUBLICATIONS

International Search & Written Opinion dated Sep. 14, 2017 in Int'l PCT Patent Appl. Serial No. PCT/IB2017/053294.

International Search Report & Written Opinion dated Mar. 29, 2012 in Int'l PCT Patent Application No. PCT/EP2012/050455.

International Search Report & Written Opinion dated Feb. 20, 2020 in Int'l. PCT Patent Application No. PCT/IB2019/057509.

International Search Report & Written Opinion dated May 17, 2021 in Int'l PCT Patent Appl. Serial No. PCT/IB2021/051698.

Johnstone, et al., Aqueous Veins and Open Angle Glaucoma, The Glaucoma Book: A Practical, Evidence-Based Approach to Patient Care, Chapter 7:65-78 (2010).

Kiel, Jeffrey W., Ocular Perfusion Pressure, IOP and the Ocular Starling Resistor Effect, The Ocular Circulation Dec. 31, 2010 (pp. 13-16).

Sponsel, et al., Retrobulbar Diversion of Aqueous Humor: Clinical Feasibility Studies, J. Glaucoma, 23(9):628-632 (2014).

International Search Report & Written Opinion dated Mar. 18, 2025 in Int'l PCT Patent Appl. Serial No. PCT/IB2024/063324.

* cited by examiner

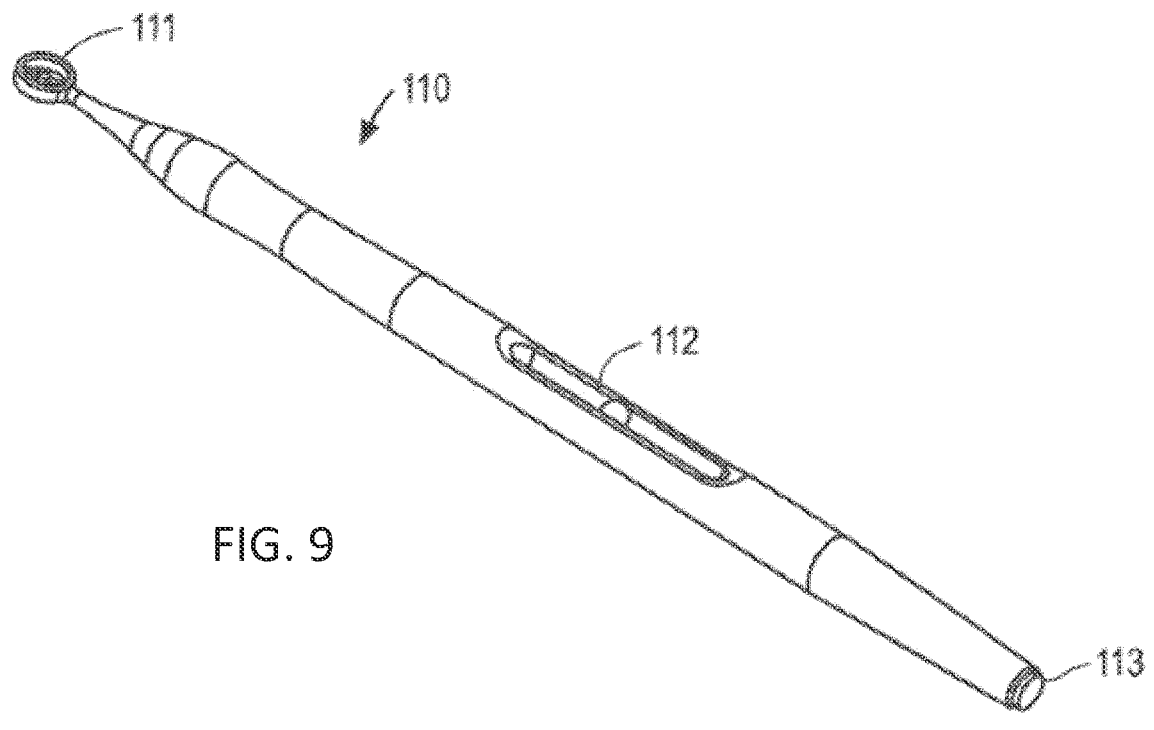
FIG. 9
FIG. 10
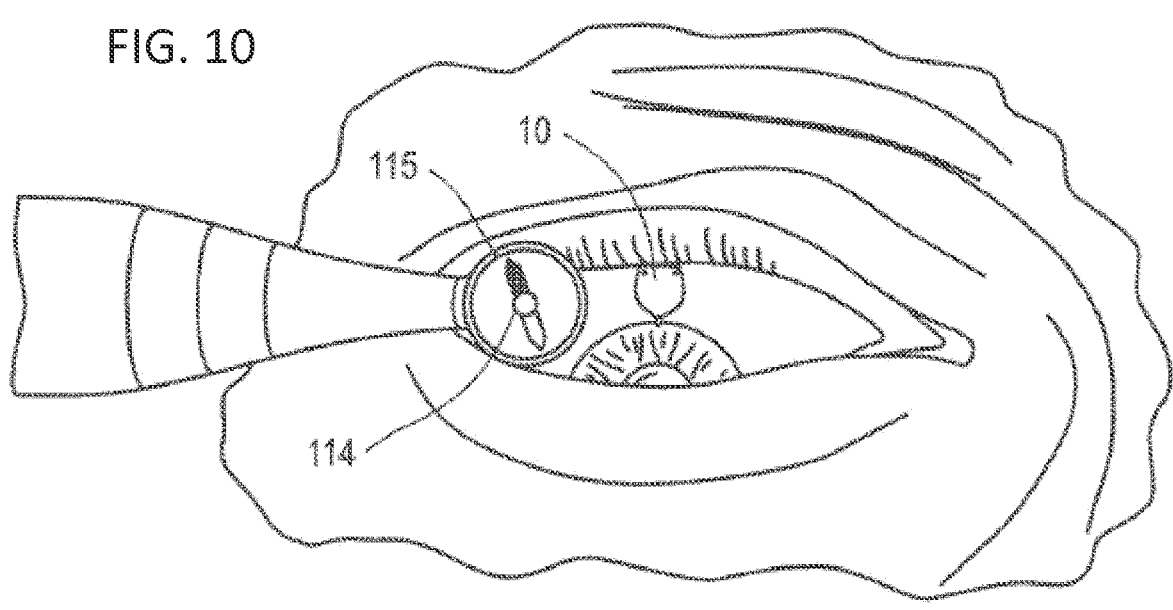

APPARATUS AND METHODS FOR TREATING EXCESS INTRAOCULAR FLUID

CROSS-REFERENCE TO RELATED APPLICATIONS

This application is a continuation of U.S. application Ser. No. 16/826,858, filed Feb. 23, 2020, now U.S. Pat. No. 11,712,371, which is a continuation of U.S. application Ser. No. 15/600,597, filed May 19, 2017, now U.S. Pat. No. 10,603,214, which is a continuation-in-part application of U.S. application Ser. No. 14/819,286, filed Aug. 5, 2015, now U.S. Pat. No. 9,655,779, which is a continuation application of U.S. application Ser. No. 13/349,353, filed Jan. 12, 2012, now U.S. Pat. No. 9,101,445, which claims the benefit of priority of U.S. Provisional Application No. 61/433,131, filed Jan. 14, 2011, the entire contents of each of which are incorporated by reference.

FIELD OF INVENTION

This application relates to apparatus and methods for draining excess intraocular fluid, for example, resulting from glaucoma.

BACKGROUND OF THE INVENTION

Glaucoma affects about 70 million people worldwide, and is a disorder associated with high pressure in the eye resulting in the generation of excess intraocular fluid (aqueous humor). Aqueous humor is produced at a rate of 2-3 μl/min by the ciliary body and it maintains constant intraocular pressure (TOP) around 12-20 mm Hg. Aqueous humor exits the eye primarily through the trabecular meshwork and Schlemm's canal, where it eventually drains to the episcleral veins. Maintaining intraocular pressure within appropriate ranges is critical to health of the eye, and depends on aqueous hunter dynamics, namely the production rate from the ciliary body (aqueous humor inflow) and its outflow rate through the trabeculum. The most frequent glaucoma is called open-angle glaucoma, and results from an increase in the fluidic resistance of the trabecular meshwork. Left untreated, this disease typically causes damage to the optic nerve, with consequent loss of vision, initially peripheral, but progressively leading to total blindness. Unfortunately, glaucoma is often asymptomatic until late in the progress of the disease.

Traditionally, glaucoma is treated using medication, for example, the daily application of eye drops, such as Brinzolamide ophthalmic, that reduce production of aqueous humor. Such medications do not cure glaucoma, and must be continue to be taken to maintain intraocular pressures within accepted limits. In certain cases, such treatment may fail and other surgical treatments are employed, such as filter procedures or placement of a glaucoma drainage device. Glaucoma drainage devices reduce intraocular fluid pressure by providing an artificial drainage pathway, thus maintaining a low intraocular pressure ("TOP").

Previously-known glaucoma drainage devices usually comprise a structure having a drainage tube that is inserted through a small incision made in the conjunctiva. The surgeon then makes a tiny incision in the sclera of the eye and creates an opening for the drainage implant device. The drainage tube is placed such that the opening of the tube is disposed in the anterior chamber of the eye within the aqueous humor. The tube is sutured in place with the drainage device attached to the sclera of the eye. Many surgeons will place an absorbable suture around the tube at the time of surgery to prevent overfiltration through the device until a fibrous capsule has formed. Accordingly, such devices typically are not functional until about 3 to 8 weeks after the procedure, so as to prevent over-filtration.

An exemplary previously-known passive glaucoma drainage device is described in U.S. Pat. No. 4,457,757 to Molteno. The device described in that patent comprises a tube of a biologically inert silicone configured to be inserted into the eye to drain aqueous humor from the anterior chamber of the eye. The device does not include a pressure regulating mechanism, but instead relies on the resistance to aqueous flow through the tubing to prevent over drainage.

One drawback of devices such as those described in the Molteno patent is that the drainage flow depends on IOP and on the fixed hydrodynamic resistance of the shunt. In many cases, however, the hydrodynamic resistance of the shunt may not be sufficient to reduce high IOP when the resistance to flow is too high, or may lead to over-drainage if the resistance is low. For example, a common problem, which arises shortly after implantation, is hypotony, which occurs when IOP drops below acceptable physiological levels (i.e., IOP<10 mmHg). Hypotony usually takes place the first few days to weeks following the implantation of a glaucoma drainage device, and is a combined result of a low fluidic resistance of both the implant and the distal outflow paths. Hypotony may lead to a number of undesirable effects and complications, such as hypotensive maculopathy, cataract formation and optic nerve edema. Another problem, also related to the fixed fluid resistance of previously known implants, is fibrosis, which appears progressively at long term and which, depending on its extend and severity, may raise the effective fluidic resistance of the implant, thereby raising the TOP to different, often non-physiological, levels.

The foregoing drawbacks have been recognized in the prior art, and several improvements have been attempted to improve flow control over the entirely passive system described Molteno.

For example, U.S. Pat. No. 5,411,473 to Ahmed describes is drainage device that includes membrane-type valve. More specifically, Ahmed describes a drainage system including a membrane folded and held in tension between two plates to provide a slit opening, such that the membrane responds to pressure changes to open or close the slit opening. Unfortunately, the operational characteristics of the system depend on the properties of the membrane, which cannot be changed easily once the device is implanted.

U.S. Pat. No. 5,300,020 to L'Esperance also describes a drainage system having a flow control element. In this patent, flow is controlled by a plug of absorbable material having porous properties that maintains anterior chamber pressure. Once aqueous humor has been absorbed into the plug, a path of relatively slow drainage flow will be established into the subconjunctival space until an equilibrium of pressures is developed. The pressure release is slow enough to avoid a collapse of the cornea yet sufficient to lower the intraocular pressure. Like the system described in Ahmed, the device described in L'Esperance includes the disadvantage that the porous material has fixed flow characteristics, and cannot be changed adapt to changes in the progression of the disease.

L'Esperance describes a further embodiment comprising a flexible drainage tube with a time-delay valve structure. The valve includes a ball biocompatible absorbable material that squeezes a portion of the drainage tube closed. As the absorbable material is dissolved by the aqueous humor, the squeezing force applied by the ball drops, progressively reducing the flow resistance of the drainage tube. In yet another embodiment, the time-delay valve comprises polymer components that either inherently, or due to the choice of composition, selectively shrink or stretch to effect opening and/or closure operation of the valve. In both of these latter embodiments, precise adjustment of the drainage flow rate is difficult to achieve, and once the valve control component has dissolved or changed shape further flow regulation is not possible.

Still other examples of previously-known systems are known. U.S. Pat. Nos. 5,626,558 and 6,508,779 to Suson describe a shunt which may be adjusted after implantation by using a low power laser to drill additional openings in the tube wall to adjust the flow rate. U.S. Pat. No. 6,186,974 to Allan et al. describes a drainage shunt having multiple layers, one of which may be a gel that swells upon absorption of fluid to adjust flow rate through the tube. U.S. Pat. No. 6,726,664 to Yaron describes a drainage tube including a distal hook that retains the distal end of the implant within the anterior chamber of the eye, and various means, such as rods or sutures, for partially occluding the lumen of the tube to regulate flow.

Other previously-known glaucoma treatment systems include significantly greater complexity to address the drawbacks of the simpler shunt systems described above. For example, U.S. Pat. No. 6,077,299 to Adelberg, et al. describes a non-invasively adjustable valved implant for the drainage of aqueous humor in glaucoma, wherein an implant having an inlet tube is surgically inserted in the anterior chamber of the eye to allow aqueous humor to flow from the anterior chamber to a valve. After passing through a pressure and/or flow regulating valve in the implant, the fluid is dispersed along the periphery of the implant to the interior of the Tenon's capsule where it is absorbed by the body. In one embodiment, the valve inhibits flow below, and allows flow above, a specific pressure difference between the intraocular pressure within the eye and the pressure within the bleb cavity in the Tenon's capsule. The specified pressure difference or set-point is always positive and the valve is always closed in the presence of negative pressure differences, to prevent reverse flow of fluid from the Tenon's capsule back into the anterior chamber of the eye.

In Adelberg, the valve is formed by a chamber to which the inlet tube is connected, such that the chamber is closed by a pressure sensitive valve in the shape of a flat cone. The pressure regulation set point of the valve is governed by a flexible diaphragm that cooperated with an armature plate having an inclined surface, and which is configured to slide over a complementary inclined surface attached to the diaphragm. Cooperation of the inclined surface of the plate and the complementary surface causes the diaphragm to deflect depending on where the armature plate is located. The armature plate is rotated, using a rotor and a set of speed-reducing and torque-enhancing gears, to regulate the flow through the device. The characteristics of the valve strongly depend on the configuration of the cone shaped valve. In addition, the regulating mechanism is complex, including many rotating parts and gears, and this complexity poses a risk of malfunction.

U.S. Pat. Nos. 6,168,575 and 6,589,198 to Soltanpour et al. describe micro-pump assemblies that may be implanted in the eye for controllably removing excess fluid to treat glaucoma. In these patents, the implantable pumps have a variable pumping rate that may be adjusted either manually or automatically, controlled by the measured intra-ocular. However, these devices have the disadvantage of being complicated and expensive. In addition, because the implantable device contains electronics and a power source, such elements must be miniaturized to fit within in a suitably small sealed enclosure. As for the device described in Adelberg, the risk of malfunction also is high due to the large number of interacting elements present that must cooperate together.

Finally, WO 2009/066133 describes an ocular drainage system including a hollow chamber coupled to a drainage tube and a disk disposed within the hollow chamber. Flow from an exit hole of the drainage tube into the hollow chamber is controlled by rotating the disk to align a variable section slit on the disk with the exit hole. Fluid passing through the exit hole and the variable section slit into the hollow chamber is released outside of the implant. Flow through the device is adjusted by magnetically coupling an external adjustment device to the disk, which enables the disk to be rotated non-invasively. A drawback of the system described in this publication, however, is that large torques may be required to rotate the disk within the hollow chamber after implantation, due to deposit of proteinaceous materials from the aqueous humor.

In view of the drawbacks of the foregoing prior at devices and methods, it would be desirable to provide an ocular drainage system and methods that are capable of being non-invasively adjusted after implantation to control the hydraulic resistance of the device.

It further would be desirable to provide an ocular drainage system having few moving parts, thereby enhancing robustness of the system and reducing the risk of failure arising from having many complex, interacting parts.

It further would be desirable to provide an ocular drainage system and methods wherein moving parts of the system are configured to reduce the risk of clogging or becoming inoperative due to the buildup of proteinaceous sediments.

Finally, it would be desirable to provide an ocular drainage system and methods that permits the hydraulic resistance of the system to be periodically adjusted in a non-invasive manner.

SUMMARY

The present invention overcomes the drawbacks of previously-known ocular drainage systems by providing an implantable device having few moving parts, and which may be non-invasively periodically adjusted to control the fluidic resistance of the device, thereby avoiding hypotony and enabling intraocular pressure to be maintained within desired limits over extended periods. In addition, the ocular drainage device of the present invention is configured so as to minimize buildup of proteinaceous sediment from the aqueous humor on moving parts of the device, thereby ensuring that the implantable device remains functional and adjustable over extended periods.

The foregoing advantages are achieved by providing an ocular drainage system comprising an implantable device and an external control unit. The implantable device includes a non-invasively adjustable valve comprising a housing that encloses at least one deformable tube and a disk rotatably mounted within the housing. The housing is configured to be implanted beneath the conjunctiva, either beneath or above the scleral surface, and includes an inlet port that communicates with the anterior chamber of the eye and an outlet port that permits aqueous humor entering the valve via the inlet port to be deposited within, e.g. a bleb formed in the sclera or a glaucoma drainage device in the form of a Seton tube, such as a Baerveldt or a Molteno device, or a flexible drainage tube having one of more drainage holes. For example, a proximal end of the flexible drainage tube may be coupled to the outlet port and a distal end of the drainage tube may be disposed in an orbital fat space of the eye such that aqueous humor entering the valve via the inlet port may be drained through the drainage tube and deposited in the orbital fat space. In another embodiment, a drainage plate may be coupled to the between the proximal and distal ends of the drainage tube. In this embodiment, the aqueous humor passing through the drainage tube exits via the plurality of drainage holes and also over the upper surface of the drainage plate into a space beneath the scleral flap.

In accordance with one aspect of the present invention, an edge of the disk bears against the deformable tube, so that a selected degree of compression may be applied to the deformable tube depending upon the extent of rotation of the disk. In one embodiment, the disk is eccentrically mounted, comprises a magnetic material or magnetizable metal alloy, and is manipulated non-invasively using the external control unit, which may comprise permanent magnets or an electromagnet. The disk preferably includes one or more ball bearings to reduce the torque required to rotate the disk after implantation. The disk optionally may include a feature that locks the disk in position to prevent inadvertent movement e.g., due to shock, and requires the application of a minimum threshold torque to adjust the rotation of the disk.

In preferred embodiments of the ocular drainage system of the present invention, the housing and disk are curved to accommodate the curvature of the eye, thereby permitting the device to be implanted under a flap formed in the sclera. In addition, the housing may include spaces that accept portions of the drainage tube(s) when the disk is rotated to compress the deformable tube to adjust flow through the device. The deformable tube may extend from the inlet port to the outlet port of the housing, or alternatively, may extend within the housing over the useful arc of contact with the disk. The outlet port may include a single or multiple openings through which fluid may exit the implantable device to the exterior of the eye. A drainage tube may be coupled to the outlet port such that fluid exits the implantable device through the drainage tube. As an alternative, a plurality of deformable tubes may be used within the housing, so that rotation of the disk within the implantable device selectively and reversibly closes off a corresponding subset of the plurality of tubes.

In accordance with another aspect of the present invention, an external control unit is provided that enables the implantable device to be non-invasively adjusted. In one embodiment, the control unit comprises a sensor for detecting the current orientation of the disk disposed within the implantable device, and one or more magnets that magnetically coupled with the disk to cause the disk to rotate through a selected angle to adjust the fluidic resistance of, and thus flow through, the device. Preferably, the control unit includes a display that provides a visual confirmation of the degree of adjustment of the implantable device.

Methods of implanting and operating the ocular drainage system of the present invention also are provided.

BRIEF DESCRIPTION OF THE DRAWINGS

FIG. 9 is a perspective view of a preferred embodiment of an external control unit of the present invention.

FIG. 10 is a perspective view depicting use of the external control unit of FIG. 9 to first determine the angular orientation of the disk within the implantable device implanted in a patient's eye prior to adjusting the angular orientation of the disk to adjust fluidic resistance of the implantable device.

DETAILED DESCRIPTION

Figure 1A:
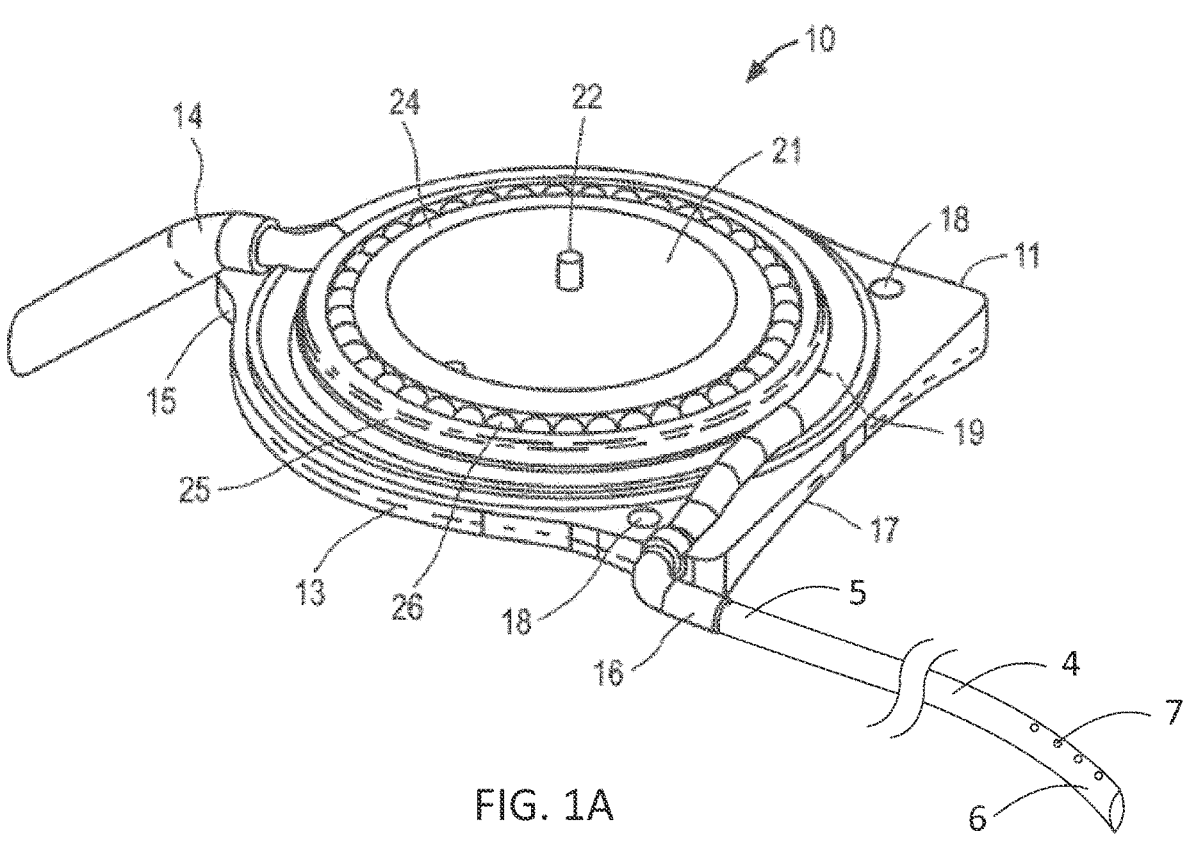
FIGS. 1A, 1B and 1C are, respectively, a perspective view an exemplary implantable device of the ocular drainage system of the present invention depicting internal components of the device in a see-through housing (FIG. 1A), illustrating the route of an adjustable fluid path within the housing (FIG. 1B), and illustrating an exploded perspective view depicting the components of the implantable device (FIG. 1C).
Figure 1B:
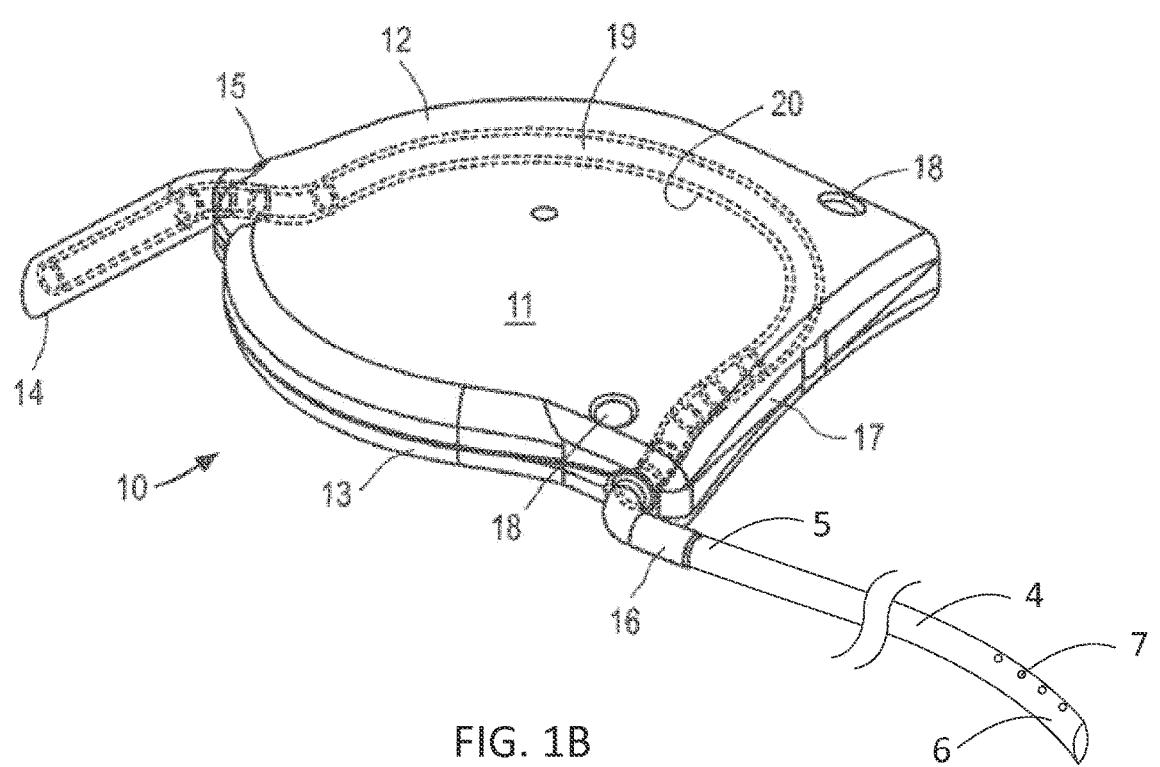

The ocular drainage system of the present invention comprises an implantable device having a valve that may be non-invasively adjusted to control the resistance to flow of aqueous humor from the anterior chamber of the eye, through the valve, and to a sink outside the eye (e.g., a bleb formed under a scleral flap or the orbital fat space of the eye). For example, as shown in FIGS. 1A and 1B, the implantable device is coupled to a flexible drainage tube having a distal end disposed within an orbital fat space of the eye and a proximal end coupled to an outlet port of the implantable device, so that aqueous humor flows from the anterior chamber of the eye, through the valve and flexible drainage tube, and is deposited in the orbital fat space of the eye. The ocular drainage system further comprises an external control unit that permits a health care provider to periodically adjust the valve within the implantable device to maintain intraocular pressures within a desired range, thereby reducing the risk of damage to the optic nerve. In accordance with the principles of the present invention, the valve may be periodically adjusted without requiring re-operation, and includes a simplified flow path that reduces the risk of clogging due to proteinaceous buildup.

An ocular drainage system constructed in accordance with the principles of the present invention is expected to provide a number of advantages over the prior art devices and methods, including:

noninvasive adjustment of fluidic resistance of the shunt over a wide range of values, thereby enabling intraocular pressure to be maintained within desired limits over extended periods of time;

the ability to provide patient-specific adjustments with a simple office visit to a clinician, by which the implantable device may be readily adjusted to apply high fluidic resistance in the early days/weeks postsurgery to avoid hypotony;

the capability to lower resistance of the shunt over the long term to compensate for increased resistance due to fibrosis at the outlet port; and simple internal mechanisms within the implantable device having with few moving parts, so that the implantable device remains functional and adjustable over extended periods of time.

Implantable Device

Figure 1C:
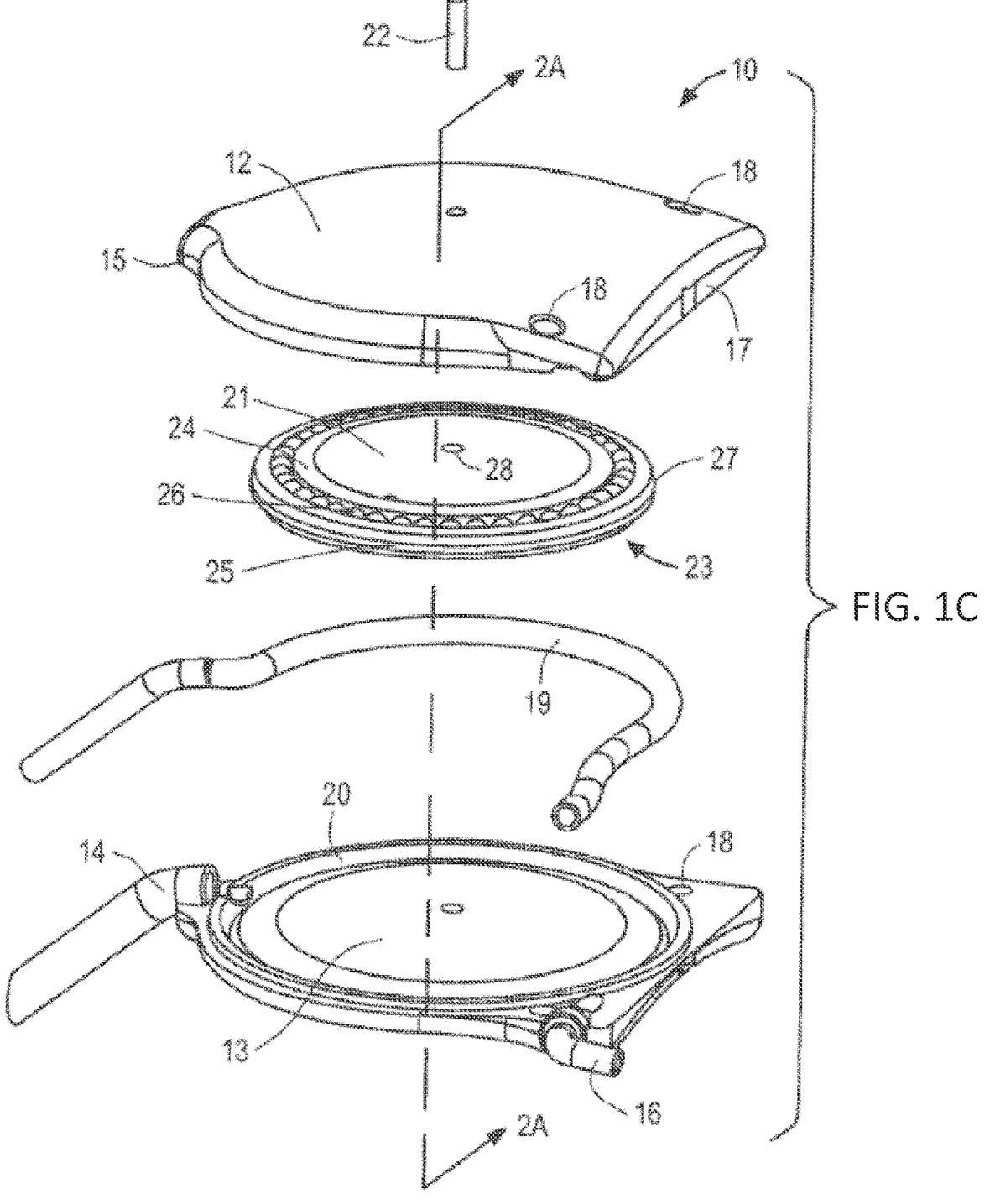

Referring to FIGS. 1A, 1B and 1C, an exemplary embodiment of the implantable portion of the ocular drainage system of the present invention is described. Implantable device 10 comprises housing 11 having upper portion 12 (for clarity omitted from FIG. 1A) and lower portion 13. Housing 11 is made of biocompatible material such that housing 11 may be implanted under the conjunctiva, either beneath or above the scleral surface. Inlet port 14 extends from proximal exterior face 15 of housing 11, while outlet port 16 is disposed near distal face 17 of lower portion 12. Inlet port 14 is configured to extend through the wall of the eye and into the anterior chamber when housing 11 is implanted on a patient's sclera. Housing 11 preferably includes eyelets 18 that enable the implantable device to be suture to the sclera to retain housing 11 in position once implanted. Fixing the implantable device with respect to the eye is important for measuring the relative position of disk 21 using the external control device, as described in further detail below.

Deformable tube 19 has a central lumen, a flow area and a corresponding fluidic resistance in its undeformed state. Deformable tube 19 extends within housing 11 and is coupled to, or extends through, inlet port 14 and outlet port 16. In a preferred embodiment, outlet port 16 is disposed at an angle of about 45° to the axis of symmetry of the implantable device (e.g., at an angle of about 225° from inlet port 14) to facilitate connection of the outlet port to a Seton tube, such as a Baerveldt or Molteno device). Deformable tube 19 is seated in groove 20 that extends along the circumferences of upper portion 12 and lower portion 13 of the housing 11 between inlet port 14 and outlet port 16.

Disk 21, which may comprise a magnetic or magnetizable material, is disposed within housing 11 on axle 22, and carries ball bearing 23 formed by inner ring 24, outer ring 25 and plurality of balls 26 captured therebetween. Ball bearing 23 ensures that the torque required to rotate the disk remains to throughout the expected useful lifetime of the implant. Outer edge 27 of outer ring 25 bears against deformable tube 19. In one embodiment, axle 22 is disposed through non-concentric opening 28 of disk 21, so that edge 27 of outer ring 25 traces an eccentric path when disk 21 rotates on axle 22. In addition, in the embodiment of FIGS. 1-3, axle 22 is located eccentrically relative to an axis of symmetry of housing 11. In this manner, rotation of disk 21 causes outer edge 27 of bearing 23 to apply to cam force to deformable tube 19, such that the amount of deformation of deformable tube 19 corresponds to the angle of rotation of disk 21.

Disk 21 preferably comprises a permanent magnet having separate poles, and a distinct axis, lying on the plane of the disk that can be sensed using a magnetic sensor. Suitable materials for disk 21 include alloys of SmCo or NdFe. As should be appreciated, non-concentric opening 28 for axle 22 is placed in disk 21 so that the magnetic axis of the disk is aligned with a preferred orientation of the disk when assembled with the other components of the implantable device, for the purposes described below. Deformable tube 19 may comprise a resilient, deformable biocompatible tubing, such as silicone, polyethylene or nylon. Alternatively, as described below, a plurality of deformable tubes may be coupled between inlet port 14 and outlet port 16, such that angular movement of disk 21 compresses and closes off a corresponding subset of deformable tubes. Housing 11 preferably is less than about 6 mm in diameter, and comprises biocompatible, waterproof or water-resistant plastic such as polyether ether ketone ("PEEK") or polycarbonate. The use of PEEK or simpler polymer is particularly desirable, as it provides long-term structural stability when implanted while also allowing for magnetic coupling between disk 21 of implantable device 10 and the magnetic field created by the external control unit, as described below. Ball bearing 23 may comprise a non-magnetic metal alloy or ceramic material, or alternatively may be made out of rubies or similar materials.

Drainage tube 4 has proximal end 5, distal end 6, and a lumen extending therebetween. Proximal end 5 may be removably coupled to outlet port 16 of implantable device 10, e.g., after implantation of drainage tube 4 and after implantation of implantable device 10. Drainage tube 4 preferably has a length such it extends from outlet port 16 and distal end 6 is disposed within an orbital fat space of the eye. Distal end 6 may include plurality of drainage holes 7 such that the lumen of drainage tube 4 may be in communication with the orbital fat space of the eye. Drainage tube 4 may be made of, for example, silicone, and may be sufficiently flexible to accommodate the curvature of the patient's eye.

Figures 2A, 2B, 3:
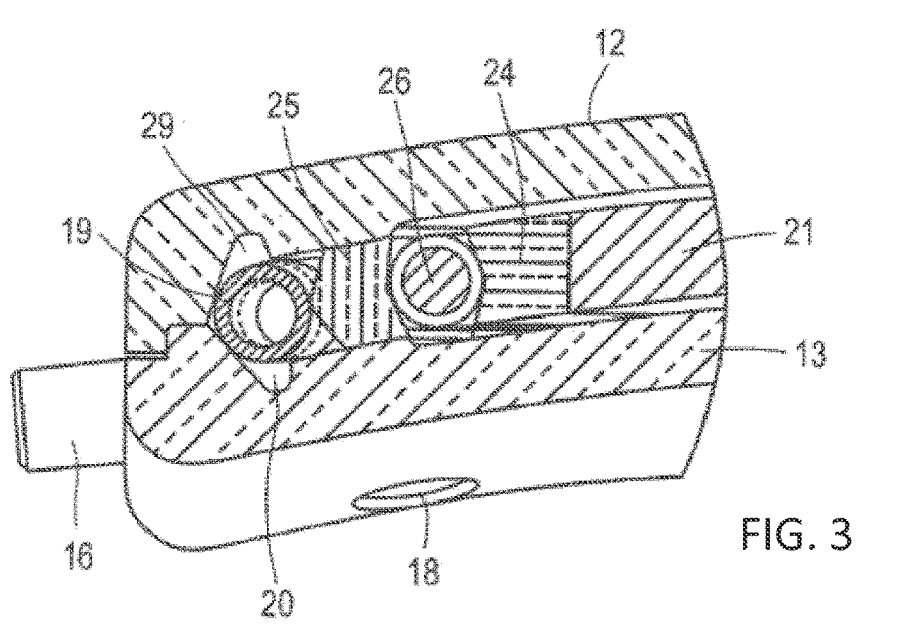
FIGS. 2A and 2B are, respectively, a side sectional view of the implantable device of FIG. 1 taken along the view line 2A-2A and a sectional view taken along view line 2B-2B. of FIG. 2A.
FIG. 3 is a detail view of a portion of the implantable device as indicated in FIG. 2A.

Referring now to FIGS. 2A, 2B and 3, further details of the components of implantable device 10 are described. FIG. 2A is a view of implantable device 10 taken along view line 2A-2A of FIG. 1B, along a plane that coincides with axis of symmetry of housing 11. Consequently, eccentrically located axle 22 is not visible in FIG. 2A. FIG. 2B provides a view at a 90° angle to that shown in FIG. 2A, and therefore passes through axle 22. As depicted in FIG. 2B, an axis A' through axle 22 preferably is displaced from the axis of symmetry A of disk 21 and of housing 11, and is thus may be rotated to a position closer to the side of the housing carrying deformable tube 19. Alternatively, axle 22 may be placed concentrically within housing 11, but instead disk 21 may have an eccentric shape so as to progressively deform deformable tube 19 when rotated about axle 22. FIG. 3 provides a magnified view of the components within call-out 3 of FIG. 2A.

Implantable device 21 is in general configured to be implanted on a sclera of the eye. The human eye is a spherical object having a radius of curvature of approximately 11 mm. Although the implantable device may be fabricated as a totally flat device, it is advantageous to have housing 11 respect the natural radius of curvature. Preferably, housing 11, disk 21 and ball bearing 23 all are constructed to have a curvature that approximates that of the human eye, so that implantable device 10 will lie snugly against the exterior of the eye, or beneath a scleral flap. In particular, implantable device 10 preferably is designed with a consistent curvature, such that the radius of curvature of the lower portion 13 of housing 11 is in a range of about 10 mm to about 12 mm, and more preferably about 11 mm. To achieve minimal thickness for the implantable device, disk 21 also should have the same curvature, as illustrated in FIGS. 2A and 2B.

Still referring to FIG. 2A, to facilitate the introduction of inlet port 14 into the anterior chamber of the eye, inlet port 14 may include rigid nozzle 30 connected to proximal face 15 of housing 11. Nozzle 30 may have a conical or sharpened extremity to facilitate piercing of the scleral tissue and introduction into the anterior chamber. Deformable tube 19 either may be placed tightly and hermetically within nozzle 30, as depicted in FIGS. 1A and 2A, or may be connected in series to nozzle 30. Nozzle preferably is inclined at angle θ with respect to the plane of lower portion 13 of housing 11 to facilitate anatomical placement of the implantable device on the sclera and insertion of nozzle 30 into the anterior chamber. Angle θ is selected to ensure that nozzle 30 does not contact or interfere with the iris when implanted, and preferably lies in the range of about 120° to 160° and more preferably about 140°.

During radial compression of deformable tube 19, the tube shortens its dimension in the plane of compression and flattens out, thereby increasing its dimension in the perpendicular plane. To facilitate the compression and deformation of deformable tube 19, grooves 20 and 29 are formed in lower portion 13 and upper portion 12, respectively, of housing, as depicted in FIG. 3. Grooves 20 and 29 accommodate lateral expansion as tube 19 flattens during radial compression, thereby reducing the resistance of tube 19 to deformation and consequently, reducing the torque required to turn disk 21 through a selected angle to compress and deform tube 19.

Figure 4:
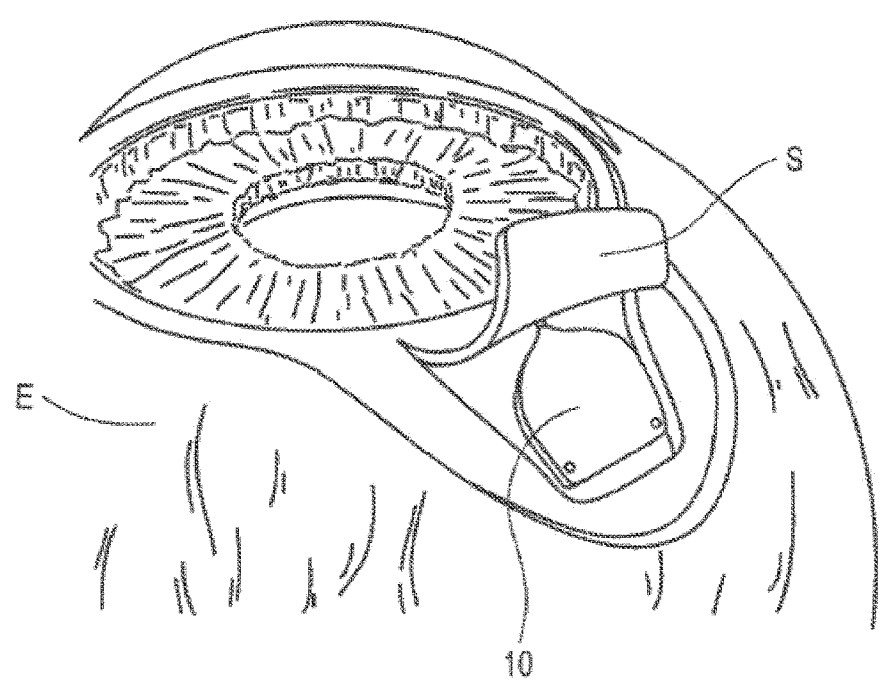
FIG. 4 is a perspective view of the implantable device of the present invention during implantation under a scleral flap formed on the exterior of a patient's eye.

Implantable device 10 is configured to be implanted within eye E under the conjunctiva, e.g., under a scleral flap S, in a manner similar to other glaucoma drainage devices, as depicted in FIG. 4. In another embodiment, implantable device 10 is configured to be implanted within eye E under the conjunctiva, e.g., above the scleral surface. In this embodiment, preferably there is a protective scleral patch disposed on top of the implantable housing to protect the conjunctival layer from device-induced erosion. Inlet port 14 drains aqueous humor from the interior of the eye, typically the anterior chamber, through deformable tube 19, to the exterior of the eye. In accordance with the principles of the present invention, the rate of drainage, and consequently, the intraocular pressure (TOP), depends on the fluidic resistance of deformable tube 19. This resistance may be adjusted by varying the degree of compression applied to deformation tube 19 by edge 27 of outer ring 25 by rotating disk 21 an axle 22, thus, e.g., reducing the flow area within the tube. Due to the eccentric location of axle 22 relative to the center of disk 21, the amount of compression applied by outer edge 27 of ball bearing 23 is a function of the angular position of disk 21.

Figure 5:
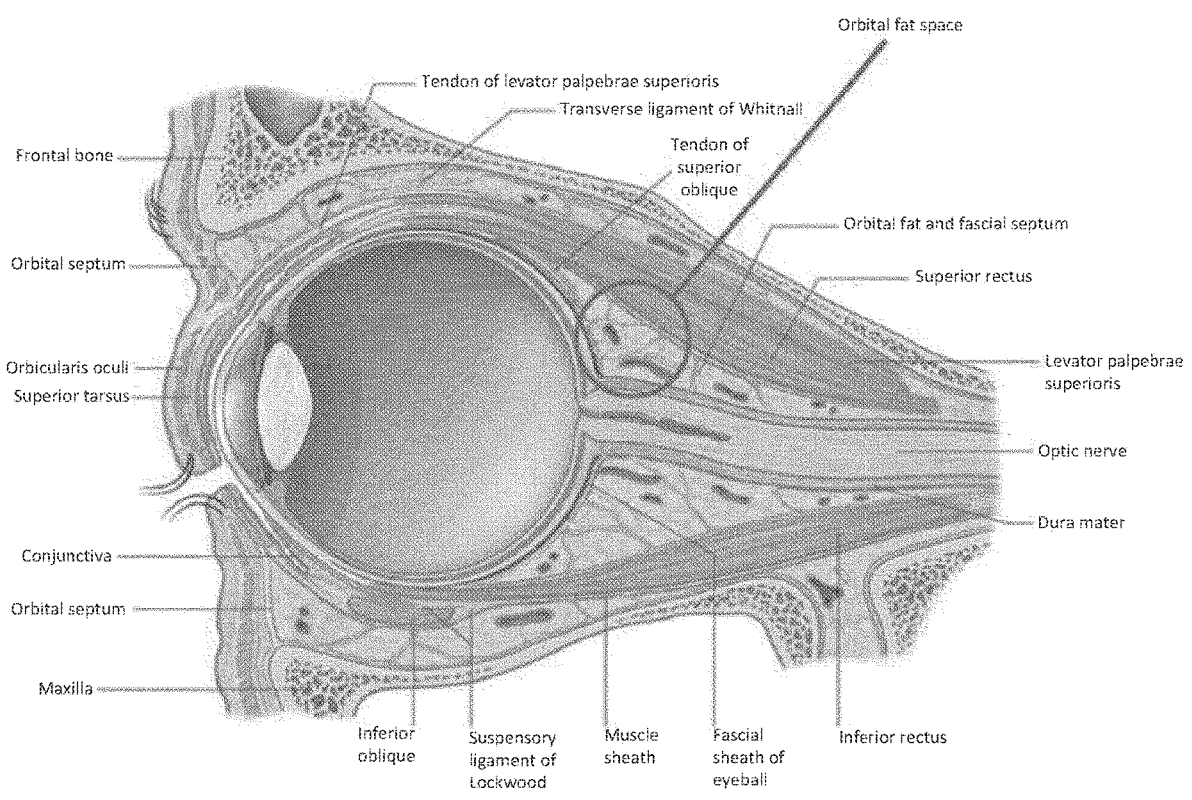
FIG. 5 depicts the structures of a human eye and the location of the orbital fat space.
Figure 6:
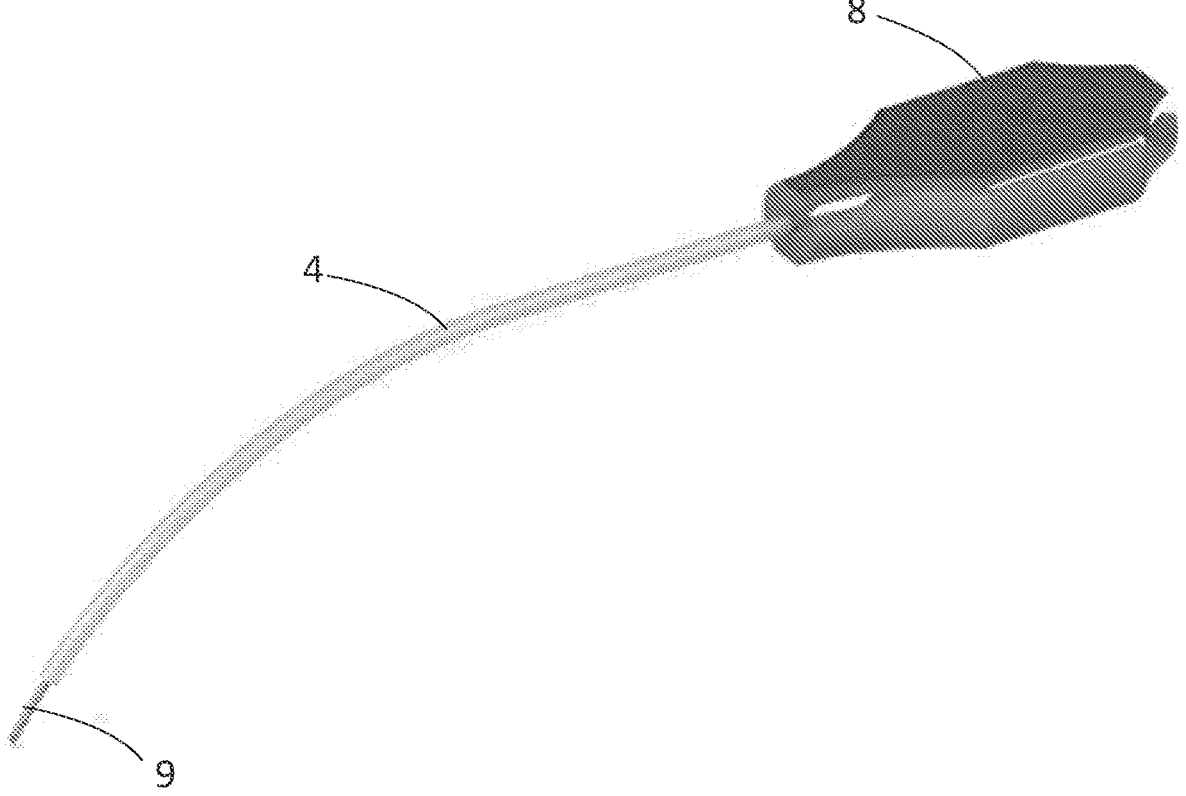
FIG. 6 depicts an exemplary embodiment of a flexible drainage tube configured to extend from the outlet port of the implantable device to the orbital fat space, wherein the drainage tube is mounted on a stylet that facilitates implantation.

Implantable device 10 may be coupled to drainage tube 4 having its distal end 6 disposed in the orbital fat space of the patient's eye, which region is depicted in FIG. 5. Accordingly, drainage tube 4 may have a length such that drainage tube 4 extends from outlet port 16 of implantable device 10 so that distal end 6 is disposed in the orbital fat space of the eye. FIG. 6 depicts drainage tube 4 disposed on stylet 9 having handle 8, which facilitates the positioning of distal end 6 of drainage tube 4 in the orbital fat space. As will be understood by persons of ordinary skill, stylet 9 is removed from drainage tube 4 after distal end 6 is positioned within the orbital fat space, and the proximal end of drainage tube 4 is then coupled to the outlet port 16 of implantable device 10. In accordance with the principles of the present invention, inlet port 14 drains aqueous humor from the interior of the eye, typically the anterior chamber, through deformable tube 19, such that the aqueous humor exits through outlet port 16 and is deposited in a cavity exterior of the eye, e.g., the orbital fat space, via one or more drainage holes 7 in the region of distal end 6.

Figures 7A, 7B, 7C, 7D, 7E:
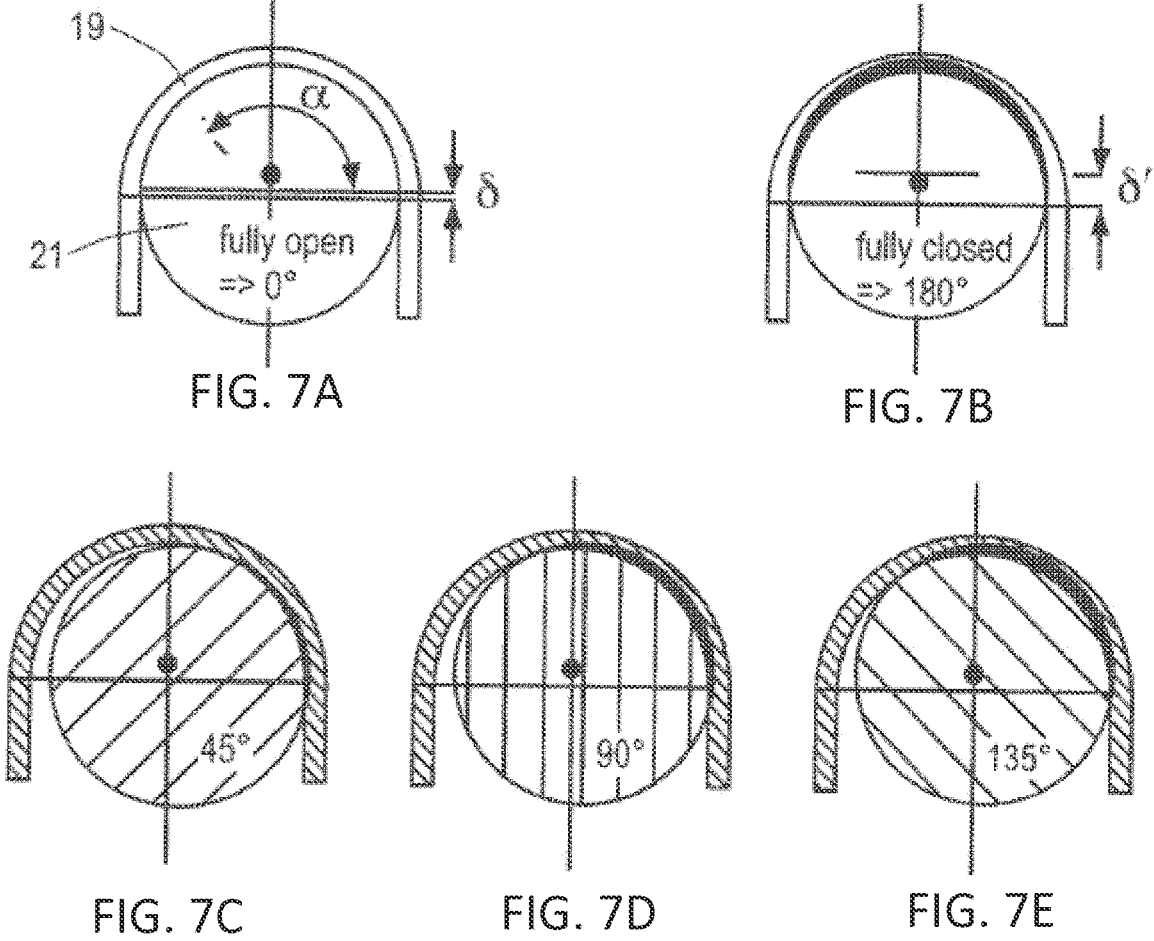
FIGS. 7A to 7E are schematic diagrams showing the amount of constriction imposed on the flow path corresponding to rotation of the disk within the implantable device through selected angles $\alpha$.

Referring now to FIGS. 7A to 7E, the angular position of disk 21 defines the extent of the zone of the tube that is compressed (shown by the darkened areas in the figures) as well as the level of compression of the tube (shown by the relative thickness of the darkened areas in the figures). FIG. 7A depicts the situation where disk 21 is at a position where angle α is 0°, corresponding to the diameter of disk 21 being parallel to the diameter of housing 11, and offset distance δ from the side of the housing containing deformable tube 19. In this position, disk 21 applies a minimum compressive force to deformable tube 19. FIG. 7B depicts the situation Where disk 21 is at a position where angle α is 180°, corresponding to the diameter of disk 21 again being parallel to the diameter of housing 11, but in this case being offset distance δ' towards the side at the housing containing deformable tube 19. In this position, disk 21 applies the maximum compressive force on the tube. FIGS. 7C through 7E depict selected intermediate angles of α at 45°, 90° and 135°, corresponding to rotation of disk 21 through 45 increments that create progressively greater constriction of deformable tube 19. In this manner, compression of deformable tube 19 may be adjusted to provide a wide range of flow restriction.

In addition, aqueous humor drained from the eye flows only through the interior of deformable tube 19, while compressive force is applied to the exterior of the deformable tube. This configuration ensures that proteinaceous materials contained within the aqueous humor passing through the valve cannot create deposits on the working parts of the adjustable valve, and reducing the risk of component failure and blockage of the implantable device.

In principle, disk 21 may be configured to act directly on deformable tube 19 such that ball bearing 23 is entirely omitted, and such a configuration represents one possible embodiment of the implantable device. However, depending on the material of which tube 19 is made, it is possible that friction and/or wear imposed on the tube by repeated adjustment of disk 21 may pose a potential failure mechanism. Accordingly, in the preceding embodiments, ball bearing 23 is employed to reduce shear forces applied to the exterior of deformable tube 19. In addition, ball bearing 23 advantageously reduces the torque required to turn disk 21. In the embodiments depicted in FIGS. 1 through 3, inner ring 24 and outer ring 25 of ball bearing 23 are especially shaped to yield a concave space there between, which confines plurality of balls 26, as shown in FIG. 3. When disk 21 is turned, inner ring 24, coupled to disk 21 turns and balls 26 roll. However, outer ring 25 need not rotate, but rather simply moves radially due to the eccentricity of the disk 21. The configuration of the embodiment depicted in FIGS. 1-3 therefore causes radial movement of outer ring 25 to compress deformable tube 19, while the absence of circumferential motion of the outer ring eliminates friction on the tube, thereby reducing torque and wear.

The implantable device of the present invention may be implanted on a sclera of the patient's eye to regulate drainage of excess intraocular fluid, and thereby regulate TOP in patients afflicted with glaucoma. Aqueous humor passing through the deformable tube and outlet port of the implantable device may exit through the outlet port, where it will be absorbed by the scleral tissue. More particularly, the fluid will be drained primarily to the connecting vein network. Alternatively, a surgeon may make a scleral flap with a large cavity beneath it (a bleb) and then make a channel to connect the implantable device to the cavity formed by the scleral flap. In this case, aqueous humor exiting the outlet port will flow via the channel to the cavity, where it will be absorbed.

In a preferred embodiment, a drainage tube may be positioned so that its distal end reaches the orbital fat space of the eye, by, e.g., using stylet 9 depicted in FIG. 6. After the implantable device is implanted on the scleral flap such the inlet nozzle of the implantable device is in communication with the anterior space, the outlet port of the implantable device is coupled to the proximal end of the drainage tube. Thus, aqueous humor exiting the outlet port will flow via the drainage tube to the orbital fat space, where it is absorbed. A scleral patch may then be applied over the implantable device and the proximal end of the drainage tube using, e.g., one or more sutures.

Figure 8:
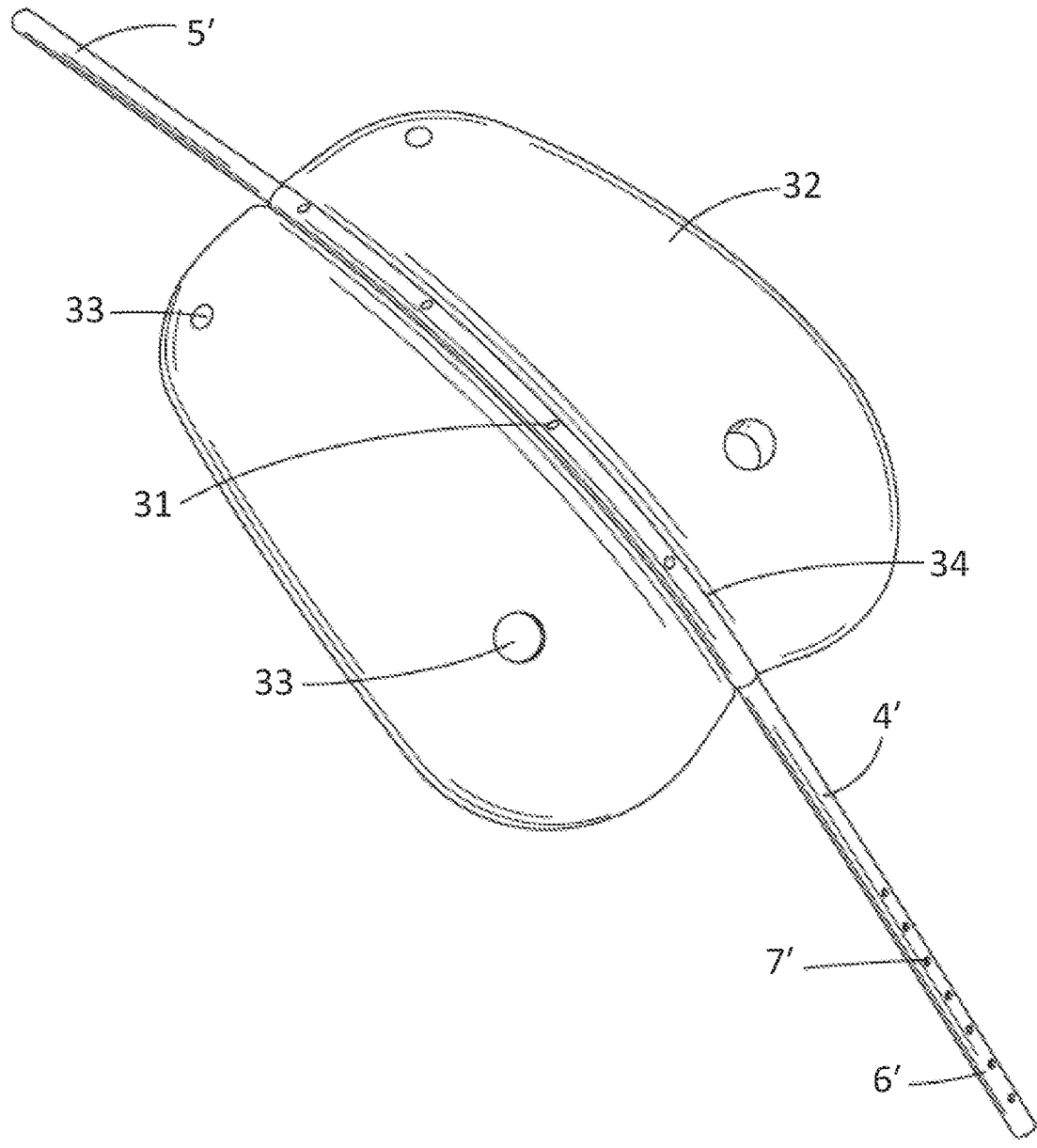
FIG. 8 is a perspective view of an alternative embodiment of a drainage tube that includes a drainage plate disposed between proximal and distal ends of the drainage tube.

Referring now to FIG. 8, in yet another embodiment, drainage tube 4' coupled to drainage plate 32 may be positioned so that drainage plate 4' is disposed on the surface of the eye such that aqueous humor may be absorbed into the scleral tissue, e.g., into the connecting vein network, and distal end 6' of drainage tube 4' is disposed in the orbital fat space of the eye such that aqueous humor may be absorbed into the orbital fat space of the eye. Drainage tube 4' of FIG. 8 is constructed similar to drainage tube 4 of FIGS. 1A and 1B. For example, proximal end 5' and distal end 6' of drainage tube 4' of FIG. 8 corresponds to proximal end 5 and distal end 6 of drainage tube 4 of FIGS. 1A and 1B, respectively, and plurality of drainage holes 7' of FIG. 8 corresponds to plurality of drainage holes 7 of FIGS. 1A and 1B. Drainage plate 32 may be curved to accommodate the curvature of the eye and may include eyelets 33 shaped and sized to permit drainage plate 32 to be implanted on an exterior surface of the eye via, e.g., sutures. Drainage plate 32 may be positioned along drainage tube 4' in between proximal end 5' and distal end 6' of drainage tube 4'. For example, drainage plate 32 may include groove 34 shaped and sized to receive drainage tube 4', and drainage tube 4' may be maintained within groove 34 via, e.g., friction or an adhesive. In this embodiment, drainage tube 4' may include plurality of drainage holes 31 along drainage tube 4' in proximity to groove 34 such that aqueous humor within the lumen of drainage tube 4' is in communication with the upper surface of drainage plate 32. Accordingly, aqueous humor that exits outlet 16 of implantable device 10 may exit via plurality of drainage holes 31 and drain over the upper surface of drainage plate 32 into the scleral tissue, and/or exit via plurality of drainage holes 7' at distal end 6' of drainage tube 4' into the orbital fat space. In this case, overall resistance of aqueous humor through drainage tube 4', e.g., due to tissue growth at either plurality of drainage holes 7' or plurality of drainage holes 31, may be maintained within a desired limit. In another embodiment, the drainage plate may be hollow such that drainage tube 4' may be positioned within the drainage plate. In this embodiment, the drainage plate may include a plurality of drainage holes along its upper surface such that the lumen of drainage tube 4' may be in communication with the upper surface of the drainage plate.

External Control Unit

Referring now to FIGS. 9 and 10, a preferred embodiment of the external control unit of the present invention is described. External control unit 110 comprises a pen-like unit including flat compass 111 at one end, optional spirit level 112 and permanent magnet 113 at the other end. Flat compass 111 is provided for measuring the orientation of the magnetic disk within the implantable device. Magnetic needle 114 of compass 111 is colored to indicate the north pole and the transparent cover or the outer rim of housing 115 contains graduations for easier reading of the angular position of the needle. Permanent magnet 113 is disposed on the other end of external control unit 110, and is used fur adjusting the angular orientation of the magnetic disk within the implantable device, as described below. Optional spirit level 112 is disposed in the main body of unit 110 and allows the user (physician) to confirm that the external control unit is in a horizontal position while measuring the magnetic disk orientation, thereby ensuring that a fixed reference frame is provided for all measurements (e.g., before and after each adjustment attempt).

A method of adjusting the fluidic resistance of an implantable device is now described with respect to FIG. 10. First, a measurement of the functional position of the magnetic disk within the implantable device is taken to determine the current angular position of the magnetic disk. With the patient seated and motionless, and with the head in a vertical position (e.g., immobilized against a typical eye examination frame), the physician pulls on the eyelid to expose the sclera. Compass 111 then is placed flat on the scleral flap, right above the implantable device, while the physician verifies that unit 110 is in horizontal position using optional spirit level 112, if provided. The angular position of compass needle 114 is noted, which corresponds to the orientation of the magnetic field emanating from the magnetic disk of the implantable device. It is expected that the magnetic disk of the implantable device will create a magnetic field in its vicinity that is orders of magnitudes greater (e.g., 150 times higher) than the magnetic field of the earth. Accordingly, the earth's magnetic field is not expected to interfere with the ability of compass 111 to accurately determine the orientation of the magnetic field of the disk within the implant.

Next, the physician turns unit 110 by 180 degrees so that the magnet (e.g., south pole) is adjacent to the sclera and near the position previously indicated by the north pole of compass 111. Positioning magnet 113 in this manner couples magnet 113 to the magnetic disk of the implantable device. The physician then moves magnet 113 in a clockwise or counterclockwise direction through a circular arc over the implantable device, causing the magnetic disk of the implantable device to rotate accordingly and increase or decrease the hydraulic resistance of the implantable device.

The physician again reverses external control unit 110 to bring the compass adjacent to the implantable device to sense the orientation of the magnetic field emanating from the implantable device. The physician may then repeat the foregoing steps a number of times until the magnetic disk within the implantable device is confirmed to have moved through a desired angle. The physician preferably then performs a measurement of IOP using a tonometer or similar device. As noted above, this test preferably is performed only after IOP is expected to have reached a new steady state (e.g., after approximately 15-30 minutes). If IOP now is within the physiological or desired range, the procedure complete. Otherwise further adjustment may be performed.

Alternative embodiments of the ocular drainage system of the present invention may include a miniaturized pressure sensor disposed with the implantable device and in communication with inlet port 14 to measure intraocular pressure. This sensor may be coupled to a miniaturized telemetry system, such as those based on radio frequency identification principles, that may be energized from distance, e.g., by circuitry on control unit 40, to emit a signal that can be received and interpreted by an external receiver. This arrangement would provide an easy and non-invasive measurement of intraocular pressure.

As a yet further alternative, a plurality of tubes may be substituted for deformable tube 19 within the housing 11. In this embodiment, rotation of the disk within the implantable device selectively and reversibly closes off a corresponding subset of the plurality of tubes, rather than simply deforming a single deformable tube 19.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method for treating excess fluid pressure within an eye, the method comprising:

implanting an inlet catheter in the eye such that an inlet end of the inlet catheter is in fluid communication with an anterior chamber of the eye;

implanting an outlet catheter in the eye, such that an outlet end of the outlet catheter is in fluid communication with a space beneath tissue of the eye;

implanting an implantable device under a conjunctiva of the eye such that the implantable device is under a scleral flap or above a scleral surface of the eye, the implantable device comprising a fluidic channel extending between and in fluid communication with the inlet catheter and the outlet catheter; and draining aqueous humor from the anterior chamber of the eye through the inlet catheter, the fluidic channel of the implantable device, and the outlet catheter to the space beneath tissue of the eye responsive to a pressure differential across the inlet catheter and the outlet catheter to thereby maintain fluid pressure within the eye within a predetermined range, wherein a rate of drainage through the implantable device is based on a fluidic resistance of the fluidic channel of the implantable device.

2. The method of claim 1, wherein the inlet catheter comprises a rigid nozzle.

3. The method of claim 2, wherein implanting the inlet catheter in the eye comprises passing an inlet end of the rigid nozzle through a wall of the eye to communicate with aqueous humor in the anterior chamber of the eye.

4. The method of claim 1, wherein the outlet catheter comprises a flexible drainage tube.

5. The method of claim 4, wherein a distal region of the flexible drainage tube comprises one or more drainage holes.

6. The method of claim 1, wherein the outlet catheter comprises a Seton tube.

7. The method of claim 1, wherein the implantable device comprises a radius of curvature selected to accommodate a radius of curvature of the eye.

8. The method of claim 1, wherein implanting the implantable device under the conjunctiva of the eye comprises implanting the implantable device above the scleral surface of the eye.

9. The method of claim 1, wherein implanting the outlet catheter in the eye comprises implanting the outlet catheter in the eye, such that the outlet end of the outlet catheter is in fluid communication with an orbital fat space of the eye.

10. The method of claim 1, wherein implanting the outlet catheter in the eye comprises implanting the outlet catheter disposed on a stylet in the eye, the method further comprising removing the stylet from the outlet catheter after the outlet catheter is implanted and the outlet end of the outlet catheter is in fluid communication with the space beneath tissue of the eye.

11. The method of claim 1, wherein draining aqueous humor from the anterior chamber of the eye to the space beneath tissue of the eye comprises draining aqueous humor from the anterior chamber of the eye through the inlet catheter, the implantable device, and the outlet catheter to be absorbed by scleral tissue of the eye.

12. The method of claim 1, wherein draining aqueous humor from the anterior chamber of the eye to the space beneath tissue of the eye comprises draining aqueous humor from the anterior chamber of the eye through the inlet catheter, the implantable device, and the outlet catheter to a connecting vein network of the eye.

13. The method of claim 1, wherein the outlet catheter is fluidically coupled to a drainage plate, the method further comprising disposing the drainage plate on a surface of the eye such that aqueous humor may be absorbed into scleral tissue of the eye.

14. The method of claim 13, wherein the drainage plate comprises a curve configured to accommodate a curvature of the eye.

15. The method of claim 1, further comprising adjusting the fluidic resistance of the fluidic channel of the implantable device to thereby maintain fluid pressure within the eye within the predetermined range.

16. The method of claim 15, wherein, in an undeformed state, the fluidic channel of the implantable device comprises a flow area and a corresponding fluidic resistance, and wherein adjusting the fluidic resistance of the fluidic channel of the implantable device comprises deforming the fluidic channel to thereby adjust the flow area of the fluidic channel.

17. The method of claim 16, wherein deforming the fluidic channel reduces the flow area of the fluidic channel.

18. The method of claim 1, further comprising coupling an inlet end of the outlet catheter to an outlet port of the implantable device to thereby fluidically couple the outlet catheter with the implantable device.

19. The method of claim 1, further comprising applying a scleral patch over the implantable device.

* * * * *